United States Patent [19]

Reeves et al.

[11] Patent Number: 5,431,054
[45] Date of Patent: Jul. 11, 1995

[54] ULTRASONIC FLAW DETECTION DEVICE

[76] Inventors: R. Dale Reeves, 5644 Westheimer #431, Houston, Tex. 77056; Thomas M. Dehoff, 3206 Gary, Spring, Tex. 77380

[21] Appl. No.: 224,262

[22] Filed: Apr. 7, 1994

[51] Int. Cl.$^6$ .................. G01N 29/10; G01N 29/26
[52] U.S. Cl. .................. 73/612; 73/614; 73/622; 73/628; 73/641
[58] Field of Search .......... 73/610, 612, 614, 620, 73/622, 624, 625, 628, 641

[56] References Cited

U.S. PATENT DOCUMENTS

| | | | |
|---|---|---|---|
| 3,720,098 | 3/1973 | Dixon | 73/620 |
| 4,305,297 | 12/1981 | Ries et al. | 73/628 |
| 4,522,064 | 6/1985 | McMillan | 73/592 |
| 4,523,468 | 6/1985 | Derkas et al. | 73/598 |
| 4,641,531 | 2/1987 | Reeves et al. | 73/622 |
| 5,165,280 | 11/1992 | Sternberg et al. | 73/622 |
| 5,189,915 | 3/1993 | Reinhart et al. | 73/623 |

Primary Examiner—Thomas P. Noland
Assistant Examiner—Rose M. Finley
Attorney, Agent, or Firm—Harrison & Egbert

[57] ABSTRACT

An ultrasonic flaw detection device including a transmitting ultrasonic transducer for producing multiple shear wave skips between inner and outer surfaces of a test object, a plurality of receiving transducers positioned ahead of and parallel to at generally the same incident angle as the transmitting ultrasonic transducer, and a processor electrically connected to the receiving transducers so as to produce a humanly perceivable indication of the reflected energy. The receiving transducers serve to receive energy of the shear wave as reflected from discontinuities in the object. Each of the receiving transducers is electronically isolated from the other receiving transducers. The receiving transducers are connected to a single channel of the processor. A fixture is provided having a first opening for detachably receiving the transmitting ultrasonic transducer and a plurality of receiving openers receiving the receiving transducers therein.

19 Claims, 4 Drawing Sheets

ULTRASONIC FLAW DETECTION DEVICE

TECHNICAL FIELD

The present invention relates to ultrasonic inspection methods and devices for performing such inspections. More particularly, the present invention relates to an ultrasonic inspection device that allows for the location of a discontinuity or flaw in a test object.

BACKGROUND ART

Ultrasonic transducers are known which have been used in pulse-echo mode to locate flaws and defects in tubular goods. In the pulse-echo mode, the ultrasonic transducer emits an ultrasonic wave and then waits to receive an echo from the defect. The angle of incidence and angle of reflection relative to the surface of the defect must be approximately equal. As a result, a transmitting transducer can only receive an echo from the defect surface which is approximately normal to the direction of ultrasonic wave transmission. If the defect surface is more than about five degrees off-normal to the direction of propagation, the ultrasonic wave will be reflected but will not return a sufficiently large component to the transmitting transducer for the defect to be detected.

Ultrasonic transducers have also been used in the past in pulse-echo mode to generate ultrasonic shear waves which travel peripherally around the tubular goods being examined, and to detect echoes reflected peripherally back to the transducer. Axially oriented ultrasonic transducers have also been used to generate axial shear waves and to detect axial echoes. For some purposes, ultrasonic transducers have been oriented perpendicular to the examined surface, for instance to determine wall thickness, and have been operated in a pulse-echo mode.

Utilizing the transmitting transducer as the detecting or pick-up transducer is commonly referred to as the pulse-echo mode. Utilizing separate transmitting and receiving transducers is commonly referred to as a pitch-catch through-transmission inspection. Each transducer commonly comprises a piezoelectric element and is mounted in a block of suitable material to form a search unit. Upon receipt of a suitable voltage spike, each piezoelectric element transmits an ultrasonic signal into a material with which the search unit is in intimate acoustical contact. Conversely, upon receipt of a suitable ultrasonic signal from the material, each piezoelectric element produces a voltage signal proportional to the pressure amplitude of the ultrasonic signal incident on the element. The amplitude and shape of the voltage signal produced upon receipt of an ultrasonic signal reflected from a particular acoustic discontinuity provides information about the discontinuity.

Prior art uses of ultrasonic inspection have utilized the receiving transducer to receive sound by placing the transmitting and receiving elements Generally facing one another and measuring signal loss due to the blockage of part of the sound wave before being received by the receiving transducer.

In any automatic ultrasonic flaw detection system, a major capital cost outlay is the area of the system's electronics for the flaw detection signal processing. The number of channels of a particular system will determine the number of transducer probes from which it can process signals. In order for an automated system to operate at high speeds, a wide scanning width is needed. This can be achieved by using large area single element probes for each channel of electronics, but the decrease in resolution of these larger probes often mandates smaller probes with a decreased inspection scan width. As a result, this increases the number of channels that a system will require for a given scan width.

In the past, various patents have issued relating to ultrasonic inspection devices and techniques. For example, U.S. Pat. No. 4,305,297, issued on Dec. 15, 1981, to Ries et al. teaches ultrasonic test equipment for testing the welding seam on a thick wall. This includes transducers arranged in tandem and along the welding seam. In this invention, a tandem pair inspects in any instance two surface-near zones (inner and outer surface) as well as an interior zone. One of the transducers of the pair participates in a function test. Two pairs of transducers cover the same zone, but from different sides.

U.S. Pat. No. 4,522,064, issued on Jun. 11, 1985, to J. D. McMillan provides an ultrasonic method and apparatus for determining the depth of cracks in a pipe or conduit. This apparatus includes a transmitting transducer and a receiving transducer which are placed on the outside surface of the pipe. The transmitting transducer is energized to direct a shear wave beam of ultrasonic energy at the crack so as to generate a complex reflected wave front from the crack. This wave front contains the information as to the size of the crack in relation to the wall thickness. The receiving transducer is moved relative to the transmitting transducer until a peak or maximum amplitude reading is found.

U.S. Pat. No. 4,523,468, issued on Jun. 18, 1985, to Derkacs et al. provides a phased array inspection of cylindrical objects. A first array of ultrasonic transducers transmits ultrasonic shear waves circumferentially around an examined cylindrical object. A second array transmits ultrasonic shear waves axially along the examined object. Triggering pulses from a triggering amplifier are switched by a multiplexer to each individual transducer of the first and second arrays. As one of the transducers assumes the role of a transmitting transducer and transmits an ultrasonic wave, the other transducers of the first and second arrays assume a receiving mode to receive reflected ultrasonic components.

U.S. Pat. No. 4,641,531, issued on Feb. 10, 1987, to Reeves et al. (one of the present inventors) describes an ultrasonic inspection apparatus for locating multiple defects in eccentric wall tubing. A plurality of transducers are arranged in mated pairs, each of the pairs including a sender element for transmitting an ultrasonic shear wave and a receiver element for receiving a reflected ultrasonic wave component from the tubular goods being inspected. Each sender element is a point focus transducer having sufficiently high resolution to maintain detectability of defects in the tubular goods.

U.S. Pat. No. 5,165,280, issued on Nov. 24, 1992, to Sternberg et al. provides a device for testing oblong objects through the use of ultrasonic waves. A transmitting ultrasonic transducer generates ultrasonic waves that are acoustically irradiated into the respective object via a coupling medium. At least three ultrasonic transducers are arranged in a row next to one another along the line. The other ultrasonic transducers are receiving ultrasonic transducers. The other ultrasonic transducers are transmitting or transmitting/receiving ultrasonic transducers. The line is inclined along the longitudinal axis of the object by an angle which is between zero degrees and forty-five degrees.

U.S. Pat. No. 5,189,915, issued on Mar. 2, 1993, to Reinhart et al. shows a single mode ultrasonic inspection method and apparatus. This is adapted to utilize both pitch/catch and pulse/echo information obtained by using a single mode of wave propagation. The apparatus includes an ultrasonic signal transmitting assembly, a signal receiving assembly, a positioning mechanism, and an arrangement for recording the information received by the signal receiving assembly. The transmitting assembly includes at least one source transducer for transmitting shear mode ultrasonic search signals into the mass of the object to be inspected. The signal receiving assembly receives shear mode ultrasonic catch signals that are produced as the ultrasonic search signals encounter discontinuities in the mass of the object to be inspected. The signal receiving assembly also receives shear mode ultrasonic echo signals that are directed back to a first source transducer.

It is an object of the present invention to provide an ultrasonic detection system that can increase the effective scan width without a significant loss of resolution.

It is another object of the present invention to provide an ultrasonic detection system that effectively increases the speed and economics of inspection.

It is a further object of the present invention to provide an ultrasonic inspection system that minimizes the number of processing channels required for inspection.

It is still a further object of the present invention to provide an ultrasonic inspection system that is easy to manufacture, easy to use, relatively inexpensive, and very accurate.

These and other objects and advantages of the present invention will become apparent from a reading of the attached specification and appended claims.

SUMMARY OF THE INVENTION

The present invention is an ultrasonic flaw detection device for detecting flaws in an object comprising a transmitting ultrasonic transducer for producing multiple shear wave skips between inner and outer surfaces of the object, a plurality of receiving transducers positioned ahead of and parallel to at generally the same incident angle as the transmitting ultrasonic transducer, and a processor electrically connected to the receiving transducer so as to produce a humanly perceivable indication of the reflected energy. The receiving transducers serve to receive energy of the shear wave as reflected from discontinuities in the object.

In one embodiment of the present invention, the transmitting ultrasonic transducer is larger than each of the receiving transducers. Also, in one embodiment of the present invention, the transmitting ultrasonic transducer serves to transmit shear waves of sufficient energy so as to saturate the test object.

The present invention provides a fixture having suitable means for positioning in proximity to the test object. The fixture has a first transmitter opening for detachably receiving the transmitting ultrasonic transducer. The fixture has a plurality of receiver openings for receiving the plurality of receiving transducers therein. The receiver openings are adjustable in linear distance from the transmitter opening. Each of the receiver openings is in linear alignment with the transmitter opening. Each of the receiver openings has a longitudinal axis in parallel relationship with a longitudinal axis of the transmitter opening.

In one embodiment of the present invention, a rear receiving transducer is positioned behind and parallel to and at generally the same incident angle as the transmitting ultrasonic transducer. The rest receiving transducer is electrically interconnected with the receiving transducers and with the processing means. Each of the plurality of receiving transducers has a center positioned adjacent exit skip points of the shear wave at the surface of the test object. The receiving transducers are positioned adjacent to the outer surface of the object at the exit skip points of the shear wave. In one embodiment of the present invention, a second plurality of receiving transducers can also be positioned adjacent an inner surface of the test object at one-half skip distances of the shear wave.

Each of the plurality of receiving transducers can be electronically isolated from the other receiving transducers/ The plurality of receiving transducers are connected to a single channel of the processor. An amplitude correction means is electrically connected to the receiving transducers so as to individually adjust a signal strength of each of the receiving transducers furthest, or attenuate those nearest, from the transmitting ultrasonic transducers. The amplitude correction means is electrically connected to each of the receiving transducers so as to correct the signal's amplitude as received by the receiving transducers.

In the present invention, the plurality of receiving transducers includes at least three receiver probes affixed in linear alignment and in parallel relationship to the transmitting ultrasonic transducer. In one embodiment of the present invention, the transmitter probe can be of a similar size as each of the receiver transducer. In another embodiment of the present invention, a rectangular transmitter transducer array is provided having a longitudinal axis parallel to the shear wave passing into the test object from the array.

The processing means can further include a gating means which is electronically connected to the transducer array of the receiving transducers so as to pass a signal exceeding a predetermined threshold value. An alarm is electrically connected to the gating means so as to produce an audio and/or visual indication relative to the signal.

As used herein, the term "channel" refers to a single channel of the flaw detector or multiple connections to a single multiplexer, the multiplexer being in turn connected to a single channel of the flaw detector.

DETAILED DESCRIPTION OF THE INVENTION

Figure 1:
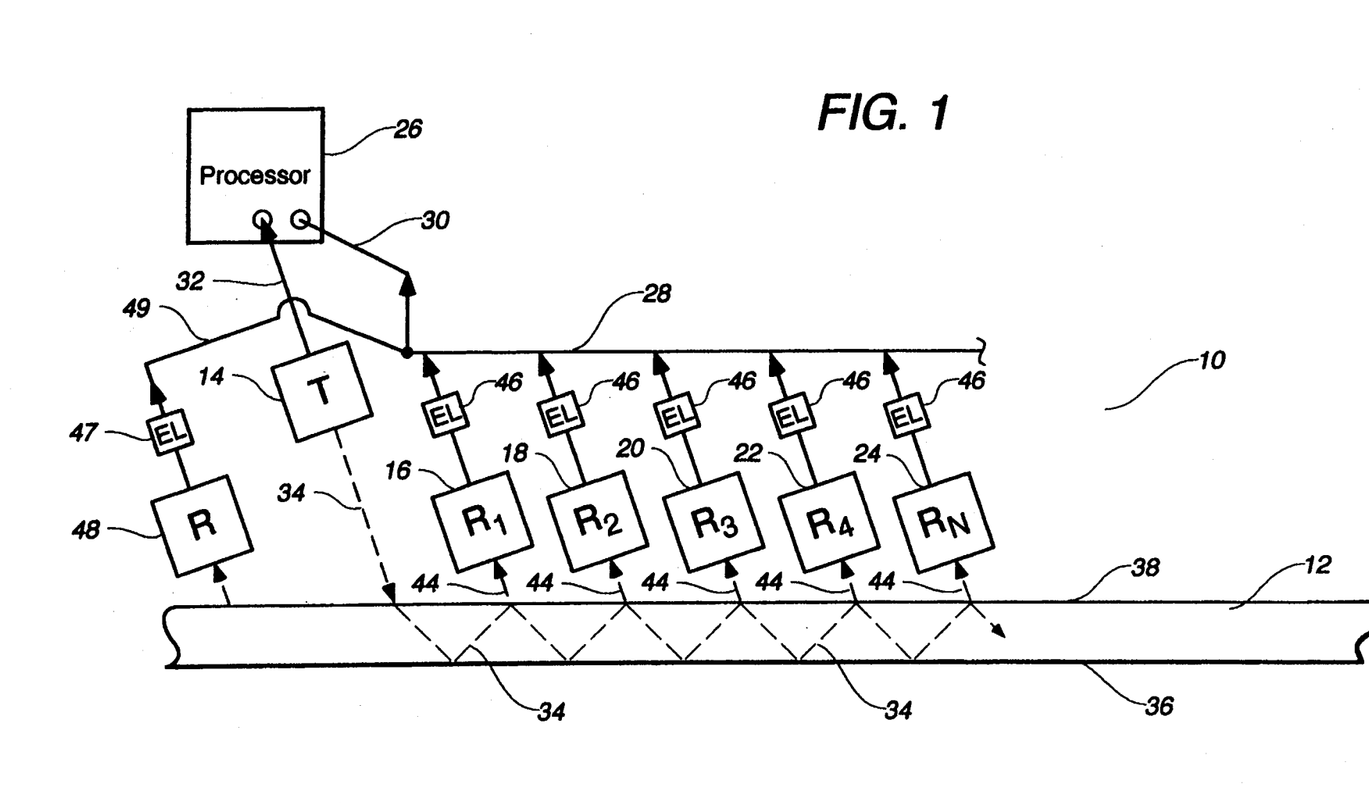
FIG. 1 is a diagrammatic illustration of the preferred embodiment of the present invention.

Referring to FIG. 1, there is shown at 10 the ultrasonic flaw detection device in accordance with the present invention. The ultrasonic flaw detection device includes a test object 12, a transmitting ultrasonic transducer 14, a plurality of receiving transducers 16, 18, 20, 22, and 24, and a processor 26. As can be seen, the plurality of receiving transducers 16, 18, 20, 22, and 24 are positioned ahead of and parallel to at generally the same incident angle as the transmitting ultrasonic transducer 14. Each of the receiving transducers 16, 18, 20, 22, and 24 are interconnected together along line 28. Line 28 is provided as a single-channel input along line 30 to the processor 26. The transmitting ultrasonic transducer 14 is connected along line 32 to the output of the processor 26.

In FIG. 1, it can be seen that the transmitting ultrasonic transducer 14 produces an ultrasonic beam with multiple shear wave skips 34 between the inner surface 36 and the outer surface 38 of the test object 12. The receiving transducers 16, 18, 20, 22, and 24 are positioned so as to receive energy as reflected from discontinuities in the material of the test object 12. Under normal circumstances, the transmitting ultrasonic transducer 14 will transmit an ultrasonic beam which is reflected between the inner surface 36 and the outer surface 38 of the test object 12. This ultrasonic beam will continue through the test object 12. Upon encountering a flaw in the test object 12, the ultrasonic beam, or a portion thereof, will be reflected from its path, as illustrated in FIG. 1. This reflected ultrasonic beam can be received by one of the receiving transducers 16, 18, 20, 22, and 24. If there is no flaw in the test object 12, then the ultrasonic beam 34 will continue along its skipping path throughout the test object 12 without sufficient reflected signal energy being received by any of the receiving transducers. If a flaw is encountered, then the reflected energy will pass into one of the receiving transducers 16, 18, 20, 22, and 24 and will pass, as a signal, to the processor 26 through lines 28 and 30.

The transmitting transducer 14 sends an ultrasonic beam 34 into the test object 12. As the ultrasonic beam 34 enters the test object 12, it will reflect off of the opposing surfaces 36 and 38 of the test object. The couplant 40 is generally a liquid material. The distance along the surfaces 36 and 38 measured from where the center line of the ultrasonic beam 34 enters the test object 12 at surface 38 to the point where it intercepts the opposite surface 36 is referred to as one-half skip. The distance measured to the intercept point on the surface 38 is referred to as one skip. The transmitting transducer 14 should be selected so as to assure that it has good transmitting qualities. A large transmitting transducer 14 will typically send a beam further and with more strength, but does not function as effectively as a receiving transducer. The transmitting transducer 14 sends an ultrasonic beam 34 through the couplant 40 and into the material 12 and the beam 34 will skip along the interior of the test object 12. If no flaw is present, the beam will continue and dissipate. If a flaw is encountered, a portion of the beam 34, depending on the size of the flaw, will be reflected back along the appropriate skip path if the flaw is approximately perpendicular to the beam path 34. The receiving transducers 16, 18, 20, 22, and 24 are positioned at the calculated skip distances along the length of the object 12.

The receiving transducers 16, 18, 20, 22, and 24 are selected for their good receiving characteristics. Typically, smaller transducers receive with better resolution than larger transducers. If the transmitting transducer 14 has a sufficiently large ultrasonic beam in comparison to the thickness of the wall of the test object 12, the material of the test object 12 will be saturated. In this case, the receiving transducers 16, 18, 20, 22, and 24 can be placed anywhere along the usable skip length without calculating the skip distances. When the receiving transducers 16, 18, 20, 22, and 24 are in place and at approximately the same incident angle as the transmitting transducer 14, and facing in generally the same direction, a reflected ultrasonic beam 44 will be received by the receiving transducer closest to the flaw and between the flaw and the transmitting transducer 14. A reflected beam 44 will continue to skip back toward the transmitting transducer 14 and will be detected by the next closest receiving transducer between the flaw and the transmitting transducer 14. It will be of reduced amplitude since the reflected beam 44 is dissipating rapidly.

The transmitting transducer 14 only sends and does not cut off to listen while the receiving transducers 16, 18, 20, 22, and 24 listen for or receive the reflection 44 from the flaw. The receiving transducers 16, 18, 20, 22, and 24 include suitable electronics 46 along their output path. The electronics 46 can serve to isolate each of the receiving transducers 16, 18, 20, 22, and 24 from the other transducers. The electronics 46 can also include a signal amplitude correction device of known electronic means. The electronics 46 are positioned before being connected, in common, and before proceeding to the processor 26. The processing equipment 26 can be electronic flaw detection equipment commonly used. The processor 26 can further include a suitable gating system which signals a defect when those signal strengths exceed a predetermined threshold value. If a gating system is used, then the processor 26 can provide an alarm electrically connected to the gating system such that the alarm produces an audio or visual indication relative to the signal.

In FIG. 1, it can be seen that there is a rear receiving transducer 48 which is positioned behind and parallel to and at generally the same incident angle as the transmitting transducer 14. The rear receiving transducer 48 is electronically interconnected along line 49 to the processor 26. The receiving transducer 48 further includes electronics 47 which can provide the necessary isolation and signal amplitude correction, or other functions so that a proper signal can be passed to the processor 26. The receiving transducer 48 is positioned so as to receive any reflections of the beam 34 which are caused by discontinuities in the test object between the entry point of the beam 34 onto the surface 38 and the first receiving transducer 16. Any such reflections will be reflected back to the transmitting transducer 14 (if it also acts as a receiving transducer) or to the rear receiving transducer 48.

Figures 2, 3:
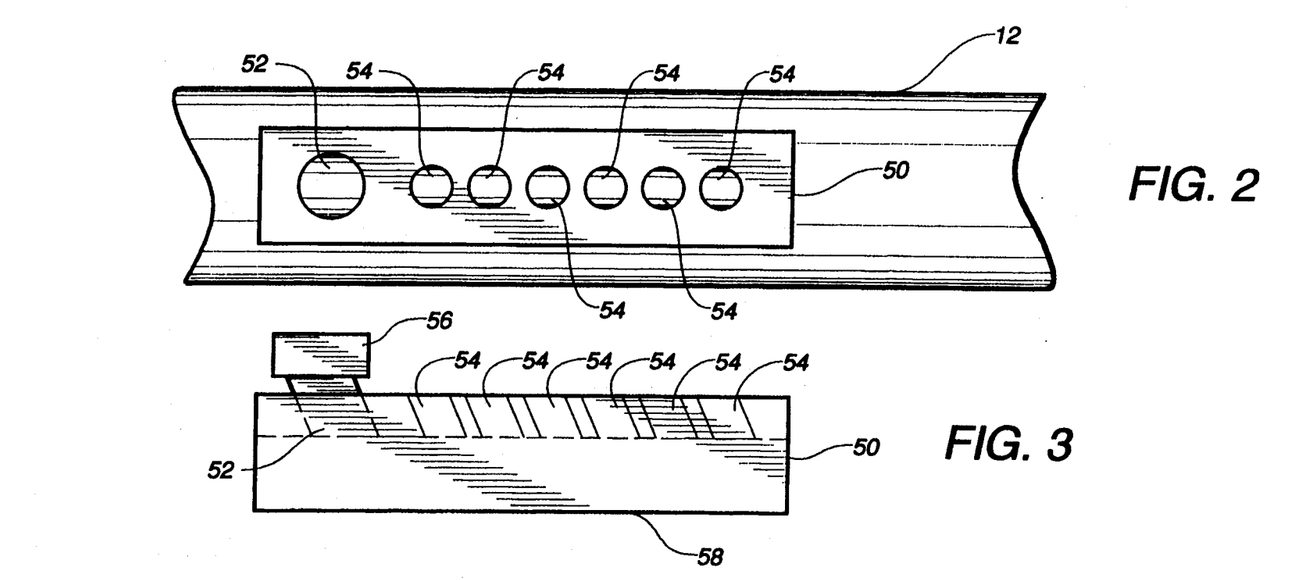
FIG. 2 is a plan view of the fixture employed by the present invention.
FIG. 3 is a side elevational view of the fixture employed by the present invention.

FIG. 2 illustrates the manner in which the receiving transducers and the transmitting transducer can be properly positioned adjacent to the surface of the test object 12. As can be seen, a fixture 50 is provided which includes a transmitter opening 52 and a plurality of receiver openings 54. In the preferred embodiment of the present invention, the transmitting transducer will be of a greater size than that of the receiving transducers. As such, the opening 52 for the transmitting transducer is of a greater size than the receiving transducers 54. The transmitter opening 52 will detachably receive the transmitter transducer therein. Similarly, the receiver openings 54 will receive receiver transducers therein. In the arrangement provided by the fixture 50, the receiver transducers will be properly positioned, in spaced relationship, relative to the exit skip points of the shear wave. Suitable and known means can be provided so as to maintain the fixture 50 at a proper distance from the surface of the test object 12. In normal use, the test object 12 may rotate as the fixture moves longitudinally along the length of the test object 12. Alternatively, the fixture 50 can be designed so as to move around the test object 12 as the test object 12 moves forward and backward longitudinally with respect to the fixture 50. It is the intended purpose of the present invention that the fixture 50 be provided so as to provide for proper scanning of the test object 12.

Figure 4:
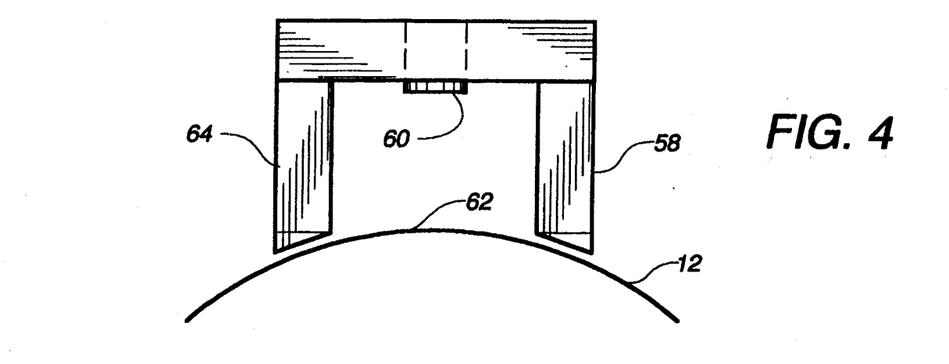
FIG. 4 is an end view of the fixture employed by the present invention.

FIG. 3 shows a side view of the fixture 50. In particular, it can be seen that the receiver openings 54 extend in parallel relationship to each other and at Generally the same incident angle as the transmitter opening 52. A receiving head 56 is provided on the transmitter opening 52 so as to properly lock a transmitter transducer in position with respect to the fixture 50. A leg 58 is provided so as to space the transmitter probe and the receiver probes a proper distance from the surface of the test object 12. FIG. 4 shows the relationship in which the leg 58 spaces the probe 60 from the surface 62 of the test object 12. Another leg 64 is provided so as to support the probe 60 in generally parallel relationship to the surface 62 of the test object 12.

Figure 5:
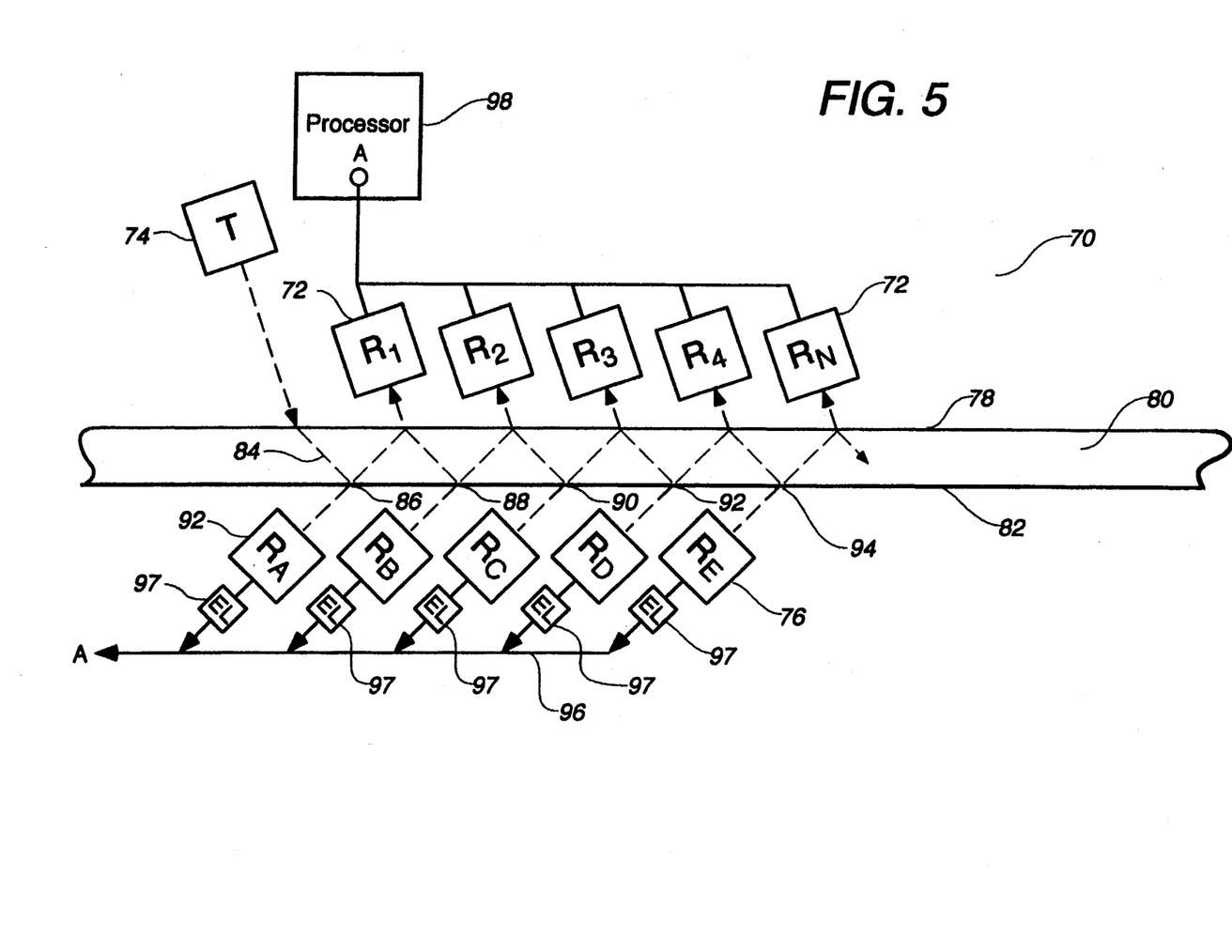
FIG. 5 is a diagrammatic and schematic view of an alternative embodiment of the present invention.

FIG. 5 shows an alternative embodiment of the present invention. For the most part, the embodiment 70, as illustrated in FIG. 5, resembles the preferred embodiment (shown in FIG. 1). However, in addition to the receiver arrangement 72 and the transmitter 74, the embodiment 70 also includes a second set of receivers 76. The first set of receivers 72 are positioned on side 78 of the test object 80. The second set of receivers 76 are positioned on the side 82 of the test object 80. In particular, the side 78 is termed herein the "outer" surface of the test object 80. The surface 82 is considered to be the "inner" surface of the test object 80. The receiver 76 includes a plurality of receiving transducers that are positioned adjacent to the inner surface 82 of the test object 80. Each of the second set of receiver transducers 76 is positioned at one half skip distances of the shear wave 84. It can be seen that the one half skip distances occur at points 86, 88, 90, 92, and 94 along the path of the shear wave 84. Each of the second set of receiving transducers 76 includes appropriate electronics 97 (as described hereinbefore relative to the electronics package 46 of FIG. 1). Each of the second set receiving transducers is connected along line 96 to the processor 98. As such, the signals from the first plurality of receiving transducers 72 and the signals from the second plurality of receiving transducers 76 pass as a single channel to the processor 98. As such, the embodiment 70 provides more thorough coverage of the testing of the test object 80. This effective scan width is maintained on a single channel without a significant loss in the resolution of the testing.

Figure 6:
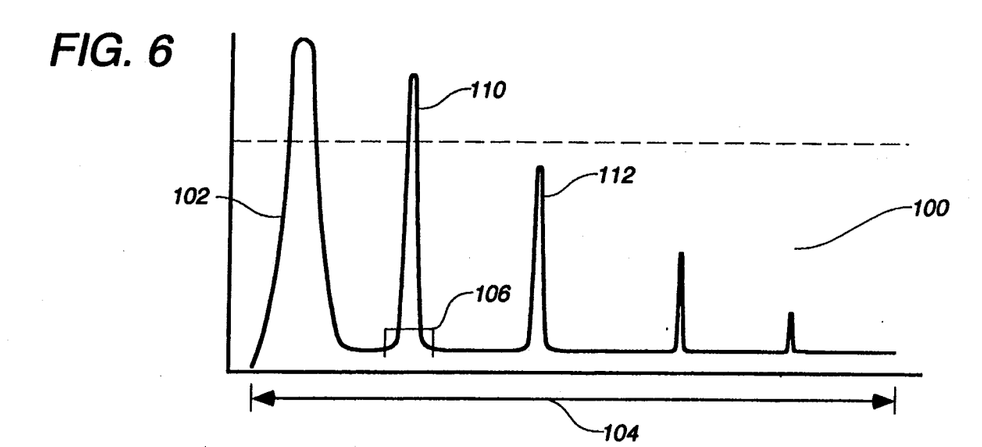
FIG. 6 is a graphical representation of signals produced in the test object.

FIG. 6 shows an analog ultrasonic flaw detector C.R.T. A-scan display image 100 of a flaw as received by a receiving transducer in a pulse-echo mode. Since the same transducer has to send/receive, a near field disturbance 102 is usually seen at the entry position of the beam. A distance 104 from left to right is the time/distance of the beam in the material. Gate 106 is located such that the largest reflected signal 110 is gated to set the alarm. Often, the largest reflected indication 110 is too close to the disturbance 102 so as to be usable. Therefore, the next largest reflected indication 112 is used.

Figure 7:
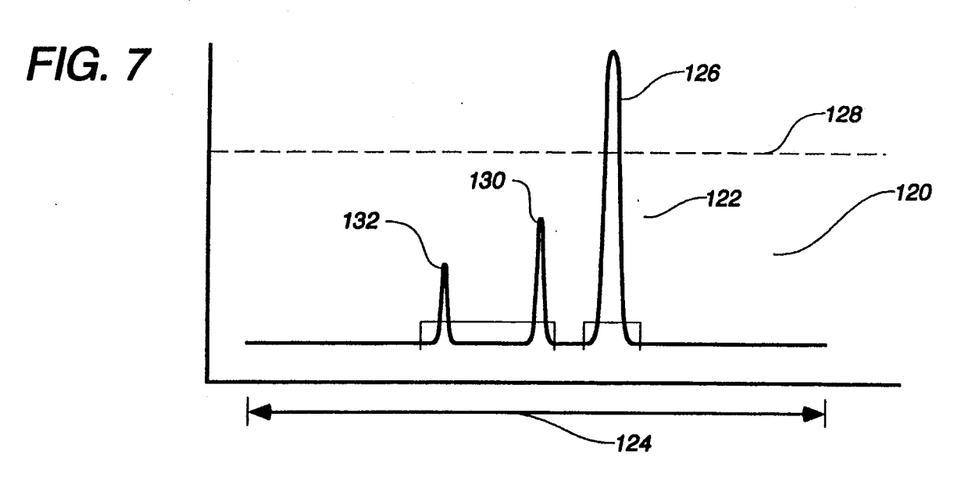
FIG. 7 is another graphical representation of signals produced from the test object.

FIG. 7 shows the C.R.T. A-scan display image 120 with a reflected indication 122 for the receiving transducers. Although an analog display is illustrated, analog and/or digital processing may be used within the scope of the present invention. Since the receiving transducers do not send, they are working out of the near field disturbance 102 and can be placed so as to receive closer to the flaw. This allows for more of the reflected beam to be detected before dissipation occurs along the skips back generally toward the transmitting transducer. In those cases where the flaw occurs under the transmitter, but before the receiver, the receiving transducer 48 can detect the reflected signal. When using the pulse-echo mode, the send/receive transducer is limited on its scan distance by near field and by dissipation of the sending/return beam. In the present invention, the usable length of the scan path 124 can be greatly increased without sacrificing sensitivity. In FIG. 7, use of the electronics package 46 can be provided so as to properly correct the signal's amplitude produced by the receiving transducers. Signal amplitude correction adjustment of receiving transducers provides individual transducer signal amplitude correction for both distance amplitude correction as well as correction for differences in individual transducer response characteristics. This adjustment causes the signals generated by all the probes from the same reflector to be perceived equal so as to enable the reliable sizing of flaws. As such, the relative proportion of the flaw indication can be properly evaluated in the graph of FIG. 7. It can be seen in FIG. 7 that the biggest flaw indication 126 would occur adjacent to the more remote receiver 22 or 24. By signal amplitude correction, the flaw indication signal will exceed the threshold value 128 so as to properly trigger the alarm. The other signals 130 and 132 relative to the closer receiving transducers 16, 18 or 20 are below the necessary threshold value. The signals 130 and 132 are the result of the dissipated reflection of the disturbance or flaw signal 126. The proper amplitude correction of the signals produced by the more distant receiving transducers can enhance the effectiveness of locating flaws and providing the proper signals to the processor 26.

The present invention contemplates the various schemes for properly transmitting and receiving the signals. For example, it is possible to transmit with the same side transmitting transducer as the receiving transducer. Under such a circumstance, it would be necessary to calculate skip intervals. It is also possible to use a sufficiently large transmitting transducer so as to saturate the material. If the material is saturated with ultrasonic energy, then it is not necessary to calculate the skip intervals. If a rectangular transmitter probe array is utilized, then the probes having their longest axis parallel to the beam axis on the material allows for saturation when the electronic pulse voltage is not sufficient to pulse a very large probe for transmission. Rectangular transmitting probes would have less element area to pulse and to allow for saturation. It is possible, within the contemplation of the present invention, to pulse with two or more small probes tied together. When the physical case size of the probes will not allow for the matching of the skip points, it is possible to stagger at every other skip point or so and to cover the gap with matching probe arrays. Such matching probe arrays can be connected to a second channel or pulsed with both arrays with one channel if it is sufficiently strong enough. It is further possible to use an array with elements built into a single case.

The present invention contemplates the use of the device on tubular sections of material or with flat or curved plates. As such, if a rectangular probe array is provided, then linear arrays of the receiving transducers 16, 18, 20, 22, and 24 can be provided in parallel relationship with a rectangular probe array. As such, a relatively large area of the plate surface can be covered. All of the probes can be properly connected along a single channel to the processor.

In order to use the present invention for oblique flaws, the receiving transducers are positioned ahead of and parallel to at generally the same incident angle as said transmitting ultrasonic transducer, but at a compound angle to said transmitting ultrasonic transducer. The first angle of the compound angle is generally the same as the incident angle of said transmitting ultrasonic transducer. The second angle of the compound angle is determined by the desired oblique flaw orientation to be scanned. This second angle is the tangent of the flaw orientation which is acute to the beam axis.

The apparatus and techniques of the present invention utilizes two or more receiving transducers so as to enhance signal response, eliminate couplant noise, and to increase inspection coverage per channel. An ultrasonic transducer, of sufficient size and frequency to cause sufficient penetration of the ultrasonic sound rays into the wall of the test object, is used to introduce ultrasonic sound waves in a certain direction into the test object, such as pipe, plate, etc. By using the through-transmission mode of standard ultrasonic transceivers, two or more receiving transducers are in line with the transmitted signal facing at generally the same direction and using approximately the same incident angle as the transmitting transducer. Instead of the sound wave having to travel out one or more skips and returning all the way back to the transmitting transducer, the receiving transducer or transducers can be placed so as to capture the sound on its return trip back after reflecting off a reflector or flaw. This allows for no new field or couplant noise since the receiving transducer does not show main bang noise. It also enhances the flaw signal response because the signal is captured close to the flaw or reflector. By using multiple receiving transducers maximized to the signal response versus distance from the transmitting transducer, coverage and signal response per each transducer channel can be enhanced. When multiple receiving transducers are used with each sending transducer, the inspection coverage of each channel is increased.

In the present invention, the signals produced by the receiving transducers are electronically isolated from each other so as to prevent feedback. The receiving signals' amplitudes are adjusted for transmitted beam attenuation through a suitable amplitude correction device. Signals from the receivers are then connected together to a single channel of an electronic ultrasonic flaw detector, thus increasing the effective scanning area per channel by a multiple determined by the number of receiving transducers ahead of the transmitting transducer.

The foregoing disclosure and description of the invention is illustrative and explanatory thereof. Various changes in the details of the illustrated configuration may be made within the scope of the appended claims without departing from the true spirit of the invention. The present invention should only be limited by the following claims and their legal equivalents.

We claim:

1. An ultrasonic flaw detection device for detecting flaws in an object comprising:
   a transmitting ultrasonic transducer means for producing multiple shear wave skips between inner and outer surfaces of the object;
   a plurality of receiving transducer means positioned ahead of and parallel to at generally a same incident angle as said transmitting ultrasonic transducer means, said plurality of receiving transducer means for receiving energy of a shear wave as reflected from discontinuities in the object; and
   processing means electrically connected to said plurality of receiving transducer means so as to produce a humanly perceivable indication of a reflected shear wave.

2. The device of claim 1, said transmitting ultrasonic transducer means being larger than each of said receiving transducer means.

3. The device of claim 1, said transmitting ultrasonic transducer means for transmitting shear waves of sufficient energy so as to saturate the object.

4. The device of claim 1, further comprising:
   a fixture having means for positioning in proximity to the object, said fixture having a transmitter opening receiving said transmitting ultrasonic transducer means, said fixture having a plurality of receiver openings receiving said plurality of receiving transducer means therein.

5. The device of claim 4, each of said receiver openings being in linear alignment with said transmitter opening, each of said receiver openings having a longitudinal axis in parallel relationship with a longitudinal axis of said transmitter opening.

6. The device of claim 1, further comprising:
   a rear receiving transducer positioned behind and parallel to and of generally the same incident angle as said transmitting ultrasonic transducer means, said rear receiving transducer electrically interconnected with said plurality of receiving transducer means and with said processing means.

7. The device of claim 1, each of said plurality of receiving transducer means having a center positioned adjacent exit skip points of the shear wave at one of the surfaces of the test object.

8. The device of claim 1, said plurality of receiving transducer means positioned adjacent the outer surface of the object at exit skip points of the shear wave, the device further comprising:
   a second plurality of receiving transducer means positioned adjacent the inner surface of the object, each of said second plurality of receiving transducer means positioned at one-half skip distances of the shear wave.

9. The device of claim 1, each of said plurality of receiving transducer means being electronically isolated from the other receiving transducer means, said plurality of receiving transducer means being connected to a single channel of said processing means.

10. The device of claim 1, said processing means further comprising:
   an amplitude correction means electrically connected to said plurality of receiving transducer means, said amplitude correction means for correcting a signal strength of said plurality of receiving transducer means.

11. The device of claim 10, said amplitude correction means comprising:

an amplifier means electrically connected to each of said plurality of receiving transducer means, said amplifier means for amplifying a signal received by said receiving transducer means.

12. The device of claim 1, said plurality of receiving transducer means comprising:

at least three receiver probes affixed in linear alignment and in parallel relationship to said transmitting ultrasonic transducer means.

13. The device of claim 12, said transmitting ultrasonic transducer means comprising:

a transmitter probe having a similar size as each of said receiver probes.

14. The device of claim 12, said transmitting ultrasonic transducer means comprising:

a rectangular transmitter probe array having a longitudinal axis parallel to the shear wave passing into the test object from said array.

15. The device of claim 1, said processing means comprising:

a gating means electrically connected to said plurality of receiving transducer means, said gating means for detecting a signal exceeding a predetermined threshold value.

16. The device of claim 15, said processing means further comprising:

an alarm means electrically connected to said gating means, said alarm means for producing an audio or visual indication relative to said signal.

17. An ultrasonic flaw detection device for detecting flaws in an object comprising:

a transmitting ultrasonic transducer means for producing multiple shear wave skips between inner and outer surfaces of the object;

a plurality of receiving transducer means positioned ahead of and parallel to at generally the same incident angle as said transmitting ultrasonic transducer means, said plurality of receiving transducer means for receiving energy of a shear wave as reflected from discontinuities in the object, each of said plurality of receiving transducer means being electronically isolated from the other of said plurality of receiving transducer means; and processing means electrically connected to said plurality of receiving transducer means so as to produce a humanly perceivable indication of a reflected shear wave, said plurality of receiving transducer means being connected to a single channel of said processing means.

18. The device of claim 17, further comprising:

a fixture having means for positioning in proximity to the object, said fixture having a transmitter opening detachably receiving said transmitting ultrasonic transducer means, said fixture having a plurality of receiver openings receiving said plurality of receiving transducer means therein.

19. The device of claim 18, each of said receiver openings being in linear alignment with said transmitter opening, each of said receiver openings having a longitudinal axis in parallel relationship with a longitudinal axis of said transmitter opening.

* * * * *